United States Patent [19]

Oschner

[11] Patent Number: 4,674,133
[45] Date of Patent: Jun. 23, 1987

[54] ULTRAVIOLET NOSE PROTECTOR

[76] Inventor: Peter B. Oschner, P.O. Box 225, Wabasha, Minn. 55981

[21] Appl. No.: 770,219

[22] Filed: Aug. 28, 1985

[51] Int. Cl.⁴ ............................................. A42B 1/18
[52] U.S. Cl. ........................................... 2/206; 2/9; 2/15; 128/163
[58] Field of Search ............... 2/206, 9, 15, 174; 128/163

[56] References Cited

U.S. PATENT DOCUMENTS

| | | | |
|---|---|---|---|
| 1,761,664 | 6/1930 | Harris | 2/206 |
| 2,527,947 | 10/1950 | Loos | 2/15 X |
| 2,572,638 | 10/1951 | Loos | 2/15 X |
| 3,068,863 | 12/1962 | Bowman | 2/15 X |
| 3,092,103 | 6/1963 | Mower | 128/163 X |
| 3,594,813 | 7/1971 | Sanderson | 2/9 X |
| 4,534,342 | 8/1985 | Paxa | 128/163 |

Primary Examiner—Henry S. Jaudon
Assistant Examiner—J. L. Olds
Attorney, Agent, or Firm—Hugh D. Jaeger

[57] ABSTRACT

An ultraviolet (UV) nose protector of a breathable material and including an adhesive on one side of the breathable material for securing all about the nose. Either the breathable material, the adhesive, or both includes a UV sun blocker, such as zinc oxide or PaBa.

6 Claims, 3 Drawing Figures

ULTRAVIOLET NOSE PROTECTOR

BACKGROUND OF THE INVENTION

1. Field of the Invention

The present invention pertains to a sun screen for an individual's nose, and more particularly, pertains to an ultraviolet nose protector for protecting the nose from sunburn and the effects of ultraviolet radiation. Particularly, the ultraviolet nose protector is intended for construction workers, sailers and boaters, hunters, outdoor persons, skiers, and any other individuals who are sensitive to the sun.

2. Description of the Prior Art

The prior art has failed to provide any nose protectors which would be cosmetically pleasing, as well as providing for blockage of ultraviolet radiation, more commonly known as sunlight. In the past, people regularly exposed to the sun, such as skiers, sailers, or construction workers by way of example, would coat their noses with creams or other solutions to prevent excessive sunburn of the nose. Sunburn and excessive exposure to the sun, of course, leads to skin cancer which has become of concern to individuals.

The prior art has failed to address a nose protector which is cosmetically appealable and protects an individual against ultraviolet radiation.

The present invention provides an ultraviolet nose protector which is cosmetically appealable and which conforms to the shape of an individual's nose.

SUMMARY OF THE INVENTION

The present invention pertains to an ultraviolet nose protector, and more particularly, pertains to a breathable material, as well as an adhesive, where either the material, the adhesive, or both contain an ultraviolet blocker. The adhesive includes an adhesive backing for being instantly affixable to the nose. The nose protector can come in a variety of sizes for either a child, teenager, or adult, as well as different configurations for different physically configured noses.

According to one embodiment of the present invention, there is provided a ultraviolet nose protector, including a member of breathable material, the member assuming a mirror image configuration including an apex, a first angled ramped side extending outwardly, a second angled side extending at a second angle at a downward slope, a third angled ramped side extending at an inward slope, and a fourth angled side again extending in a downward slope to a flat bottom. An adhesive is secured to one side of the breathable material, the adhesive allowing for breathing of the skin as well, and includes a removable backing of a smooth material. The breathable material, the adhesive, or both can include a sun blocker, such as PaBa or zinc oxide, providing for absorption of ultraviolet rays from 2 to 15 on the spectrum scale for ultraviolet absorption.

One significant aspect and feature of the present invention is a ultraviolet nose protector which is cosmetically pleasing and unnoticeable to the naked eye. The nose protector can be of either a clear material or of various flesh colored materials, depending upon a person's particular skin pigment makeup.

Another significant aspect and feature of the present invention is a nose protector which blocks the sun and protects the nose accordingly. The nose protector is pleasing and sightly to an individual, and provides for the necessary protection to the outdoors person, such as a skier, a sailer, or a hunter.

Another significant aspect and feature of the present invention is a nose protector which is cosmetically pleasing and easily applicable by any individual. The nose protector is suited towards the sports-minded individual and provides for protection. Particularly it lends itself in application to individuals who wear glasses, such as sun glasses or regular glasses for corrective eyesight.

Having thus described one embodiment of the present invention, it is the principal object hereof to provide an ultraviolet nose protector for protecting an individual's nose from the rays of the sun.

One object of the present invention is to provide a cosmetically pleasing ultraviolet nose protector which protects one's nose from the sun in the ultraviolet spectrum scale of 2 to 15, dependent upon the amount of ultraviolet blocker in either the material, the adhesive, or both.

Another object of the present invention is to provide a nose protector which is non-irritating to an individual's nose; and, also of a physical, mental, and medical benefit.

DESCRIPTION OF PREFERRED EMBODIMENTS

Figure 1:
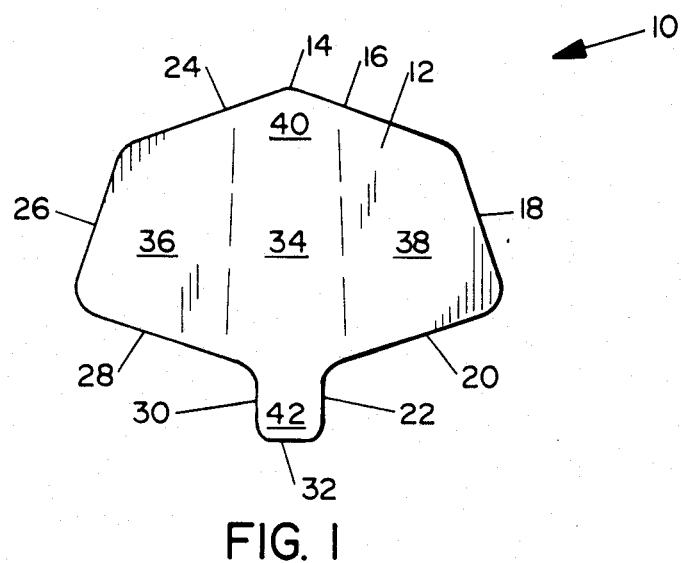
FIG. 1 illustrates a plan view of an ultraviolet nose protector, the present invention.

FIG. 1 illustrates an ultraviolet nose protector 10, the present invention, including a member of breathable material 12 such as cloth or plastic and assuming a predetermined, geometrical configuration in mirror image. The geometrical configuration includes an apex 14, a first angled side of a ramped outward slope 16, a second angled side of a downward slope 18, a third angled side of an inward ramped slope 20, and a fourth angled side of a downward slope 22. The slopes 16 and 20 are opposite to each other while the slopes 18 and 22 can be about equal. Likewise, there are mirror image sides 24, 26, 28, and 30, respectively. The sides 22 and 30 join to a substantially flat bottom member 32. All the sides are continuously connected. There is an apex portion 40 and center portion 34, which cover the arch of the nose; side portions 36 and 38, which cover the sides of the nose; and a bottom portion 42, which covers the bottom of the nose in between the two nostrils of the nose. The member 12 is of a breathable material, such as a cloth material or a breathable synthetic material, providing for passage of moisture outwardly from the nose, as well as for breathing of the skin. The material 12 is coated with an adhesive 44 and covered with a plastic backing material 46. Either the breathable material 12, or the adhesive 44, or both, can include an ultraviolet sun blocker, such as zinc oxide or PaBa (paraamino benzoic acid) in the spectrum scale of 2–15 for ultraviolet absorption. The adhesive is also breathable.

Figure 2:
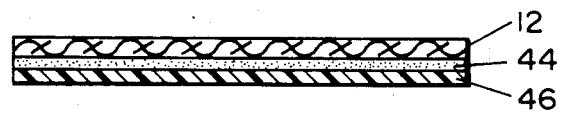
FIG. 2 illustrates a side view.

FIG. 2 illustrates a side view of the present invention where all numerals correspond to those elements previously described.

MODE OF OPERATION

The ultraviolet nose protector 10 is applied to the nose in four steps. First, the backing material 48 is removed. Second, the arch of the nose is covered with the area 34 of the nose protector 10. Third, the sides 36 and 38 are positioned against the sides of the nose. Fourth, the bottom portion 42 is positioned down over the bottom of the nose in between the nostrils, providing for vertical placement between the apex portion 40 and the bottom portion 42 with respect to the side placement 36 and 38 and with respect to the sides of the nose. Of course, the nose protector peals off the nose in a like fashion in reverse order of the steps.

The nose protector 10 can be of a color corresponding to an individual's skin and complexion, such as flesh color and of course dependent upon an individual's skin pigment makeup and can be made of a shiney reflective surface to reflect heat away from an individual's nose, or can be of a flat non-reflective color if reflection of light rays into the eye is a consideration. The nose protector can also be provided with decorative symbols, such as stars, sunbursts, lighting strikes, the symbol of the sun, or even a specific name, such as the name of a sailboat. Also, the nose protectors can be provided in the specific colors of the sailboat, such as if the hull of the sailboat is red, the color of the nose protector would likewise correspondingly be red. Further, the name of the sailboat could be printed on to the face of the nose protector either vertically or horizontally. Of course, sailboats are not limiting as any type of a vehicle or vessel name could be applied.

Figure 3:
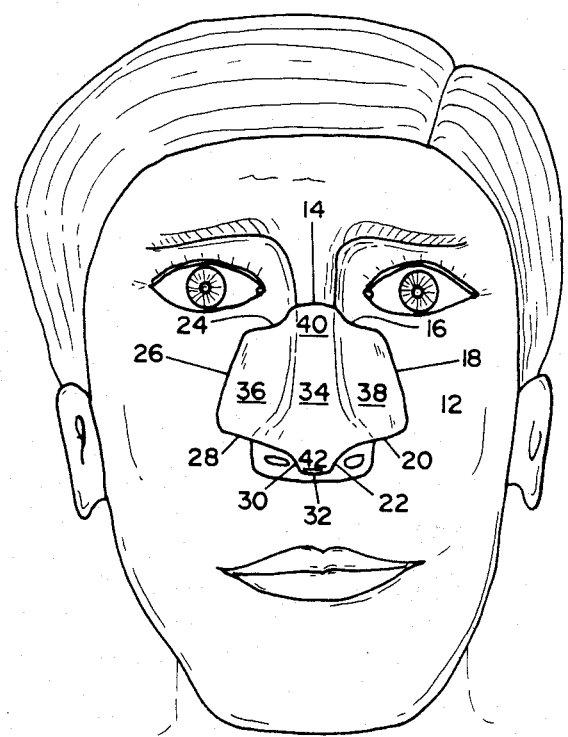
FIG. 3 illustrates the ultraviolet nose protector on an individual's nose of a wearer.

FIG. 3 illustrates the ultraviolet nose protector on the individual's nose where all numerals correspond to those elements previously described.

What is claimed is:
1. Nose protector of substantially two dimensions for conforming to the three dimensional facial surfaces of an individual's nose comprising:
   a. breathable material means conforming to the facial surfaces of an individual's nose and including a geometrical mirror image configuration of an uppermost apex, a first outward ramped slope, a second angled downward slope, a third inward ramped slope, a fourth angled downward slope, and a bottom forming a continuous side thereabout;
   b. adhesive means affixed to said breathable material means;
   c. backing material affixed to said adhesive means; and,
   d. ultraviolet blocking means included in at least said breathable material means or said adhesive means for blocking ultraviolet energy and radiation, whereby said uppermost apex affixes about the bridge of the nose, said first, second, third and fourth slopes affix to the side of the nose, and said bottom affixes to the surface separating said nostrils, thereby protecting the nose from ultraviolet energy and radiation.

2. protector of claim 1 wherein said breathable material means contains said ultraviolet blocking means.

3. Nose protector of claim 1 wherein said adhesive means contains ultraviolet blocking means.

4. Nose protector of claim 1 wherein said material means and said adhesive means contain said ultraviolet blocking means.

5. Nose protector of claim 1 wherein said ultraviolet blocking means is zinc oxide.

6. Nose protector of claim 1 wherein said ultraviolet blocking means is PaBa.

* * * * *